(12) United States Patent
Wang et al.

(10) Patent No.: US 6,178,808 B1
(45) Date of Patent: Jan. 30, 2001

(54) APPARATUS AND METHOD FOR TESTING THE HYDRAULIC CONDUCTIVITY OF GEOLOGIC MATERIALS

(75) Inventors: Xiaodong Wang, Madison; Craig H. Benson, Verona, both of WI (US)

(73) Assignee: Wisconsin Alumni Research Foundation, Madison, WI (US)

( * ) Notice: Under 35 U.S.C. 154(b), the term of this patent shall be extended for 0 days.

(21) Appl. No.: 09/372,970

(22) Filed: Aug. 12, 1999

(51) Int. Cl.$^7$ .................................................. G01N 15/08
(52) U.S. Cl. .................................................................. 73/38
(58) Field of Search ..................................... 73/38, 37, 73, 73/74, 152.05, 861.46, 385

(56) References Cited

U.S. PATENT DOCUMENTS 2,618,151 * 11/1952 Leas .......................................... 73/38
6,055,850 * 5/2000 Turner et al. ............................. 73/38

FOREIGN PATENT DOCUMENTS

1268577 * 6/1961 (FR) .

OTHER PUBLICATIONS

"Permometer P700000 Instruction Manual," (Jul. 1995), 14 pgs., Trautwein Soil Testing Equipment, P.O. Box 31429, Houston, TX 77231.
"WCC—Clifton Laboratory Test Procedure for Permeability Test wtih Backpressure Using Constant Vol.—Falling–Head Apparatus,"(Apr. 1981), 7 pgs.
L. Bjerrum and J. Huder, "Measurement of the Permeability of Compacted Clays,".
Proceedings of the Fourth International Conference on Soil Mechanics and Foundation Engineering, London, vol. 1, Div. 1a/2, pp. 6–8, Aug. 1957.

* cited by examiner

Primary Examiner—Hezron Williams
Assistant Examiner—Michael Cygan
(74) Attorney, Agent, or Firm—Quarles & Brady

(57) ABSTRACT

A method for measuring hydraulic conductivity of geological samples using a closed volume pumping system that ensures constant volume of test liquid within the sample and a shaped tube of mercury to provide a constant pressure difference across the sample to eliminate second order influences on the hydraulic conductivity measurement and to speed measurement.

12 Claims, 1 Drawing Sheet

APPARATUS AND METHOD FOR TESTING THE HYDRAULIC CONDUCTIVITY OF GEOLOGIC MATERIALS

STATEMENT REGARDING FEDERALLY SPONSORED RESEARCH OR DEVELOPMENT

This invention was made with United States government support awarded by the following agencies: NSF Grant No. 9800255. The United States has certain rights in this invention.

CROSS-REFERENCE TO RELATED APPLICATIONS

BACKGROUND OF THE INVENTION

The invention relates generally to geological test instruments, and, in particular, to instruments for detecting how well fluids are conducted through geological materials such as clays, rocks, and soil.

The hydraulic conductivity of geological materials is important for determining their drainage capacity and the mobility of liquids such as oil or water in subsurface strata. The hydraulic conductivity of less permeable geological media may be less than $10^{-4}$ cm/sec.

Measurement of such hydraulic conductivities presently entails placing the sample in a test cell so that liquid flow may occur only between an inlet and outlet opening in the cell. Tubing connects the openings to burettes containing the test fluid, typically water. The burettes have adjustable heights and graduation lines so that the column heights of the contained fluid may be easily measured.

In the "fallinghead risinghead" method of measuring hydraulic conductivity, the water level in one burette is placed above the water level in the other to establish a pressure differential across the sample and the rate of flow measured by comparing, at periodic intervals, the changing heights of the liquid columns in the burette.

In the "fallinghead" method, only one burette is used and the remaining opening in the test cell drains into a graduated cylinder or similar device.

In both methods, the burettes are typically open to the air. However, they may be closed and pressurized, for example with compressed air, to achieve a greater pressure difference. This pressurization addresses the problem that steady state hydraulic flow necessary to establish conductivity can take many hours or weeks to occur.

In a "constant volume" method originally described by Bjerrum, L. and Huder, J., in their publication *Measurement of Permeability of Compact Clays*, Proc. 4$^{th}$ Intl. Conf. on Soil Mech. and Foundation Eng., 1957, a closed loop is established between the inlet and outlet to and from the test sample so that the test sample always has a constant volume of test fluid. A falling column of mercury incorporated into this closed loop provides the pressure difference across the test sample. While this method has decreased measurement times (by decreasing the time to steady state hydraulic conductivity where inflow equals outflow), the test results can still take many hours or days to stabilize.

All of these methods have produced erratic results if insufficient time is allowed for stabilization to occur.

BRIEF SUMMARY OF THE INVENTION

The present invention provides a test of hydraulic conductivity suitable for geological materials, but where test results are obtained in minutes rather than hours and where variations in the measurements are much reduced.

In the invention, a closed loop of test fluid is maintained with constant pressure differential. A "constant head mercury column" is used to provide constant differential pressure in a closed loop environment ensuring a constant fluid volume in the sample.

Specifically, the present invention provides a method for testing geological materials for hydraulic conductivity including the steps of enclosing the sample material in a cell having fluid impermeable walls and a first and second opposed port separated by the sample. The geological sample is saturated with a test fluid and placed under a constant pressure difference across the first and second ports while fluid flow of the test fluid through the ports is matched so that a constant volume of test fluid is within the sample.

It is thus a principal object of the invention to eliminate variations of pressure difference in a closed loop system such as may affect the stability of the measurement of geological materials of complex characteristics. Although the inventors do not wish to be bound to a particular theory, it is believed that the changing pressure difference inherent in prior art constant volume devices may unpredictably influence the measurement by changing, the hydraulic gradient in the sample, the pore water pressure and the stress on the sample. By providing a constant pressure difference, as well as a constant volume of test fluid in the sample, these and other second order effects on the measurement of hydraulic conductivity are eliminated.

The greater stability in the measurement further shortens the necessary measurement time.

The constant pressure difference across the first and second ports may be ensured by the use of a tube, a portion of which is filled with a material of greater specific gravity than the test fluid. A vertically oriented portion of this tube is completely filled with the material of greater specific gravity and connects at its upper end with horizontal tube at partially filled with the material of greater specific gravity. An interface exists separating the material of greater specific gravity from the test fluid. The free ends of the tube are attached one to each of the first and second ports.

It is thus another object of the invention to provide a means for producing a constant pressure difference across the sample that may be used in a closed loop and that is compatible with the goal of a constant volume of fluid flow. The vertically oriented flexible tube may be part of a constant volume connection between the first and second ports that ensures the same fluid flow into the first port as out of the second port. The horizontal tube, which adds no hydraulic head to the hydraulic head already applied by vertically oriented flexible tube, is used to measure the volume of fluid flow The connections between the vertically oriented tube and the horizontal tube and the first and second orifices may provide interfaces between the material of greater specific gravity and the test fluid and these interfaces may have an identical cross- sectional area.

Thus, it is another object of the invention to eliminate the effect of pressure drop caused by meniscus capillary pressure of the various fluids.

One interface between the material of greater specific gravity and the test fluid may be an upwardly extending tube terminating in an orifice of a predetermined cross-section and surrounded by a well.

Thus, it is another object of the invention to provide a connection between the material of greater specific gravity and the test fluid that is both fixed in height and of a predetermined and constant cross-sectional area.

The foregoing and other objects and advantages of the invention will appear from the following description. In the description, reference is made to the accompanying drawings which form a part hereof and in which there is shown by way of illustration a preferred embodiment of the invention. Such embodiment does not necessarily represent the full scope of the invention, however, and reference must be made to the claims herein for interpreting the scope of the invention.

DETAILED DESCRIPTION OF THE INVENTION

Components of the Control System

Figure 1:
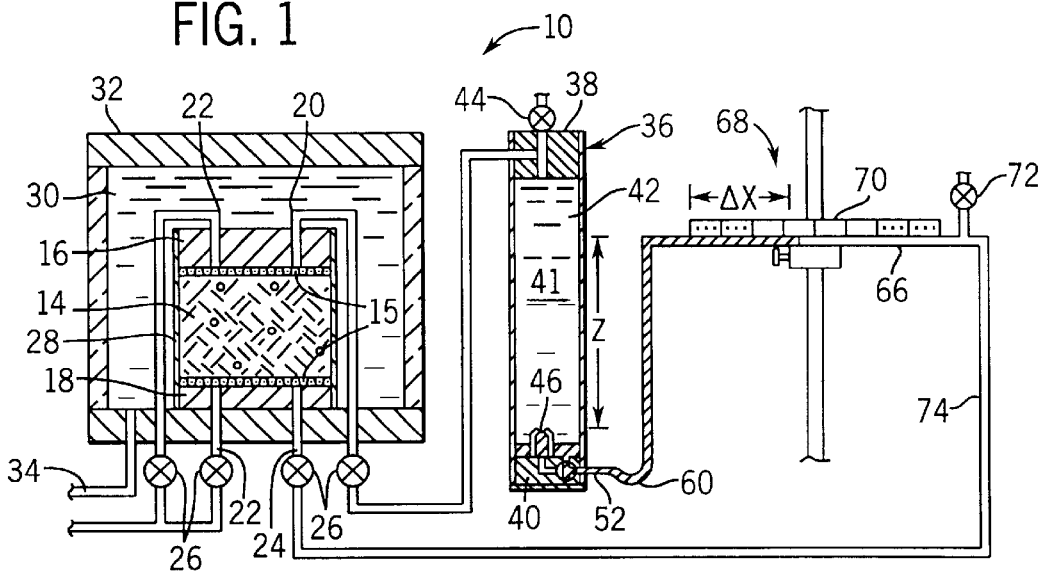
FIG. 1 is a cross-sectional view of an apparatus suitable for use with the present invention showing a test cell incorporating a geologic material connected to an interface chamber in turn driven by a bent column pressure source.

Referring now to FIG. 1, test apparatus 10 suitable for use with the present invention includes a test cell 32 holding a sample 14 of geological material of generally cylindrical dimensions with parallel upper and lower ends.

The ends of the sample may be covered with a diffuser 15, such as a layer of geofabric, which acts to allow free fluid flow and distributes the flow along the ends of the sample and thus pressure equalization at the ends.

Abutting the diffusers 15 are parallel, rigid upper and lower end caps 16 and 18. Upper end cap 16 includes an inlet port 20 and a first saturation port 22 whereas lower end cap includes an outlet port 24 and a second saturation port 22. Each of the inlet port 20, the outlet port 24, and the saturation port 22 have separate valves 26 which may be opened to allow passage of test fluid through the various ports or closed to block that passage.

The upper and lower end caps 16 and 18 are commensurate with the bases of the sample 14, extending only to the edge thereof, where they join to and are joined by a cylindrical flexible membrane 28 enclosing the sample 14 on its sides with the upper and lower end caps 16 and 18 covering the sample's top and bottom.

The membrane 28 is fluid impermeable and is compressed against the sides of the sample 14 by the pressure of a fluid bath 30 contained in a closed cell 32 surrounding the sample, membrane, and end caps. Pressurization of the cell 32 may be accomplished by cell pressurization line 34. When the membrane 28 is thus compressed, fluid flow between the inlet port 20 and the outlet port 24 must be through the sample 14 and not along its outer edges.

The inlet port 20 is connected to a mercury separator 36 consisting of a vertical tubular column capped at its upper and lower ends by plugs 38 and 40, respectively, and partially filled with the working fluid of the test, typically water 41. The inlet port 20 connects through valve 26 to a passage in the upper plug 38 providing a Tconnection, one branch of which connects to the top of a water column 42 and the other branch of which connects through a bleed valve 44 to the atmosphere. The bleed valve 44 is used to remove any air from the system, such as will naturally migrate to the top of the water column 42 during set-up.

Figure 2:
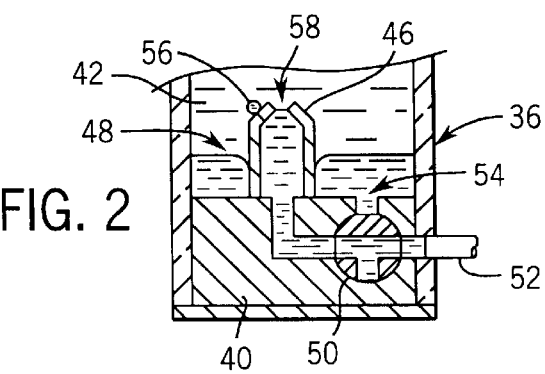
FIG. 2 is a detailed view of the material interface of FIG. 1.

Referring now to FIGS. 1 and 2, the lower plug 40 supports an orifice tube 46 extending upward into the water column 42, the outer walls of which provide about the orifice tube 46 a well 48. The orifice tube 46 connects through lower plug 40 to an internal Tvalve 50, which may alternatively connect separator inlet 52 to the orifice tube 46 or to a well drain 54 at the bottom of the well 48.

During operation of the test, when the valve 50 is in a first position shown in FIG. 2, water will be forced from the water column 42 through the sample 14 by the introduction of mercury through separator inlet 52 into orifice tube 46. The mercury so introduced forms beads 56 which promptly fall into the well 48, thus displacing water 41 but preserving a constant cross-sectional area of interface 58 between the water and mercury. As will be described below, this cross-sectional area is matched to a second interface between mercury and water in a capillary tube so as to provide a balancing between meniscus forces at this interface such as might upset an accurate measurement of pressure difference between the inlet orifice 20 and the outlet orifice 24. It will be understood that other materials than mercury and water may be employed., However, the high specific gravity of mercury with respect to water provides an extremely compact instrument.

When the valve 50 is in the second position, not shown in FIG. 2 but shown in FIG. 1, mercury may be drawn from the well 48 through the well drain 54 back out of separator inlet 52 for a resetting of the test apparatus 10.

Referring now again to FIG. 1, separator inlet 52 may be connected by a vertically oriented flexible tube 60 to the horizontal tube 66, which is a capillary tube. The flexible tube 60 is such as to provide constant internal volume during testing and thus may be, for example, a malleable metal tube of small internal diameter that may be flexed for bending yet that will maintain a constant volume during operation of the test. The vertical separation distance between the end of the orifice tube 46 and the horizontal tube 66 is the vertical height Z. The height Z and the specific gravity of the mercury within the orifice tube 46 and vertically oriented flexible tube 60 determines the pressure difference across the sample 14. The flexure of flexible tube 60 allows adjustment of the height of the horizontal tube 66 such as will determine a pressure difference across sample 14. Note, generally flexible tube 60 is flexible yet not expansive or compressible, and which thus may facilitate easy hook up of tube 66 and the separator 36.

The upper end of the flexible tube 60 connects with a horizontal tube 66 partially filled with mercury to provide a second mercury water interface at end 68. The horizontal tube 66 may be a capillary tube of small diameter to accentuate movement of the end 68 of the column of mercury as may be measured against a scale 70 extending along horizontal tube 66 with flow through the flexible tube 60 into the inlet port 20. The rate of flow may be determined by a measurement of a distance x whereas the volume of flow will be $\Delta x$ times the cross-sectional area ol the capillary of horizontal tube 66. At the far end of the horizontal tube 66 with respect to its connection with vertical tube 60 is a bleed valve 72 whose operation will be explained shortly and a connection with a return tube 74 which connects through valve 26 to the inlet port 20.

Figure 3:
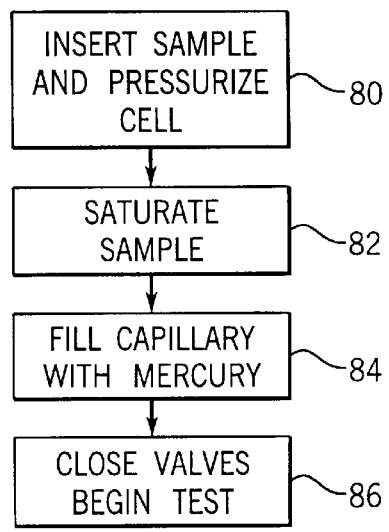
FIG. 3 is a flow chart showing the steps of operation of the device of FIG. 1.

Referring now to FIGS. 1 and 3, at a first step 80 in a test procedure using this apparatus 10, the sample 14 is placed within the test cell 32 and the cell is pressurized through the introduction of pressure into cell 32 thus pressing the flexible membrane 28 tightly against the sample 14.

Next, at process block 82, the sample is saturated by an opening of valves 26 associated with the saturation ports 22 to saturate the sample 14 with the working fluid, typically water. At this time, valves 26 associated with the inlet and outlet ports 20 and 24 are closed. The fluid entering through the saturation ports 22 infuses the sample and dissolves small amounts of gas within the sample.

After a suitable period of time, valves 26 associated with the inlet ports 20 may be opened followed by an opening of valve 44 to bleed out any gas within the separator 36. As indicated by process block 84, valve 44 is then closed and bleed valve 72 is opened with valve 50 (shown in FIG. 2) connected to the well drain 54 causing mercury to flow backward out of separator inlet 52 up vertical flexible tube 60 and along horizontal tube 66. When the mercury-test fluid interface 68 reaches the end of the scale near bleed valve 72, bleed valve 72 is closed. Sufficient mercury is placed in well 48 so that no water is introduced into flexible tube 60. At this time, valves 26 associated with the saturation orifices 22 are closed and valves 26 associated with the inlet and outlet ports are opened. Valve 50 is set to connect separator inlet 52 with orifice tube 46 (as shown in FIG. 2) as indicated by process block 86 and the test may begin.

At the start of the test, the water 42 from the separator 36 is forced through inlet ports 20 by the weight of the mercury in the column of flexible tube 60 with the weight of mercury in horizontal tube 66 having no effect, but the end 68 of the tube indicating a volume flow through the sample. Hydraulic conductivity is computed from the readings on the capillary of horizontal tube 66 using a modified form of the constant head equation. If head loss within the tubing is negligible, then fluid mechanics shows that the difference between the water pressure at the inlet port 20 and outlet port 24 is:

$$u_i - u_o = Z(G_{Hg} - 1)\gamma w + L \quad (1)$$

Where $u_i$ is the inlet water pressure at inlet port 20, $u_o$ is the outlet water pressure at outlet port 24, Z is the elevation difference between the tip of orifice tube 46 and the center of the horizontal tube 66, $G_{Hg}$ is the specific gravity of mercury (13.54 at 23° C.) and L is the thickness of the sample 14 measured between the end caps 16 and 18. Equation (1) ignores the net capillary pressure drop caused by the water mercury menisci as may be done because the orifice size of the tube 46 equals the capillary size of horizontal leg 66.

Inspection shows that the drop in elevation across the sample 14 cancels when the drop in total head is calculated, thus by applying Darcy's Law, the hydraulic conductivity is computed as follows:

$$K = \frac{a_c L}{AZ(G_{Hg} - 1)} \left(\frac{\Delta x}{\Delta t}\right) \quad (2)$$

Where $\Delta x$ is the horizontal displacement of end 68 during a time $\Delta t$ and $a_c$ is the cross-sectional area of the capillary tube. Equation (2) is simpler than that required using other techniques.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

We claim:

1. A method of testing geological materials for hydraulic conductivity comprising the steps of:

(a) enclosing a sample geologic material in a cell having fluid impermeable walls, the cell including a first and second opposed orifice separated by the sample geologic material;
    (b) saturating the sample geologic material with a test fluid;
    (c) placing a constant pressure difference across the first and second orifices while matching fluid flow of the test fluid passing into the first orifice and out of the second orifice to provide a constant volume of test fluid within the sample geological material, wherein the placing step comprises providing a vertically oriented tube having a constant height and filled with a material of greater specific gravity than the test fluid, the vertical tube being joined at its upper end with a horizontal tube partially filled with the material of greater specific gravity, the free ends of which are attached one each to the first and second orifices, and wherein the weight of the material of greater specific gravity material in the vertical column provides the constant pressure difference; and
    (d) measuring the rate of fluid flow through one of the first and second orifices to deduce hydraulic conductivity through the geological material.

2. The method of claim 1 wherein the test fluid is water.

3. The method of claim 1 wherein the geologic sample is selected from a group consisting of rock cores, compacted clay, bariner soils and geosynthetic liners.

4. The method of claim 1 wherein the step of saturating the geological sample simultaneously introduces pressurized test fluid through the first and second orifices.

5. The method of claim 1 wherein the constant volume of test fluid within the sample is ensured by connecting the first and second orifices together in a closed loop of fixed internal volume.

6. An apparatus for testing the hydraulic conductivity of geological materials to a test fluid, the apparatus comprising:

(a) a cell sized to receive the sample geologic material and having fluid impermeable walls pierced by a first and second opposed orifice positioned to be separated by the sample geological material when so positioned;
    (b) a constant volume constant pressure pump connected between the first and second orifices and operating so as to match fluid flow passing into the first orifice and out of the second orifice to ensure a constant volume of test fluid within the sample geological material, wherein the pump includes a tube having a constant height vertical tube filled with a material of greater specific gravity than the test fluid, the vertical extending tube joined at its upper end to a horizontal tube at least partially filled with the material of greater specific gravity than the test fluid, the free ends of which are attached one each to the first and second orifices by connecting lines; and
    (c) a flow monitor producing a measurement of the rate of fluid flow through one of the first and second orifices whereby hydraulic conductivity through the sample geological material may be deduced.

7. The apparatus of claim 6 including in addition, a source of pressurized test fluid and a valve for introducing the pressurized test fluid into the cell to saturate the sample geological material when so positioned.

8. The apparatus of claim 6 wherein the test fluid is water and wherein the material of greater specific gravity is mercury.

9. The apparatus of claim 6 wherein the connections between the bent column and the first and second orifices provide regions of interface between the material of greater specific gravity and the test fluid, and wherein these regions are of identical cross sectional area;

whereby meniscus forming capillary pressure drop between the fluids is canceled.

10. The apparatus of claim 9 wherein the region of interface between the material of greater specific gravity and the test fluid of the vertically extending leg is an upwardly extending tube terminating in an orifice of predetermined cross section, the tube surrounded by a well.

11. The apparatus of claim 6 wherein the flow monitor is a transparent capillary tube and scale.

12. The apparatus of claim 6 wherein the vertically extending leg includes a height adjustment means.

* * * * *

UNITED STATES PATENT AND TRADEMARK OFFICE
CERTIFICATE OF CORRECTION

PATENT NO. : 6,178,808 B1  
DATED : January 30, 2001  
INVENTOR(S) : Xiaodong Wang et al.

Page 1 of 1

It is certified that error appears in the above-identified patent and that said Letters Patent is hereby corrected as shown below:

Column 4,
Line 57, "ol" should be -- of --.

Column 5,
Line 55, "At" should be -- Δ --.

Signed and Sealed this

Fourth Day of December, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.      : 6,178,808 B1
DATED           : January 30, 2001
INVENTOR(S)     : Xiaodong Wang et al.

Page 1 of 1

It is certified that error appears in the above-identified patent and that said Letters Patent is hereby corrected as shown below:

<u>Column 4,</u>
Line 57, "ol" should be -- of --.

<u>Column 5,</u>
Line 55, "At" should be -- $\Delta$t --.

This certificate supersedes Certificate of Correction issued December 4, 2001

Signed and Sealed this

Seventeenth Day of September, 2002

*Attest:*

*Attesting Officer*

JAMES E. ROGAN
*Director of the United States Patent and Trademark Office*